United States Patent [19]

Gordon

[11] Patent Number: 5,043,101

[45] Date of Patent: Aug. 27, 1991

[54] FERROMAGNETIC, DIAMAGNETIC OR PARAMAGNETIC PARTICLES USEFUL IN THE DIAGNOSIS AND TREATMENT OF DISEASE

[76] Inventor: Robert T. Gordon, 4936 W. Estes, Skokie, Ill. 60077

[21] Appl. No.: 174,694

[22] Filed: Mar. 29, 1988

Related U.S. Application Data

[63] Continuation-in-part of Ser. No. 464,870, Feb. 8, 1983, abandoned, and a continuation-in-part of Ser. No. 559,229, Dec. 8, 1983, abandoned, which is a continuation-in-part of Ser. No. 731,551, May 7, 1985, Pat. No. 4,735,796.

[51] Int. Cl.$^5$ .................. G01N 31/00; A61K 37/14; C07K 17/10; C08B 37/02
[52] U.S. Cl. .................. 252/408.1; 424/1.1; 424/9; 514/6; 514/59; 534/11; 534/12; 534/15; 534/16; 530/400; 436/518; 436/529; 536/113
[58] Field of Search .............. 252/408.1; 424/1.1, 424/9, 85.8, 86; 514/6, 59; 436/523, 528, 529, 518; 128/653 A, 659; 534/11, 12, 15, 16; 536/113; 530/400; 600/3

[56] References Cited

U.S. PATENT DOCUMENTS

| 4,018,886 | 4/1977 | Giaever | 424/12 |
|---|---|---|---|
| 4,106,488 | 8/1978 | Gordon | 424/1.1 |
| 4,136,683 | 1/1979 | Gordon | 424/1.1 |
| 4,303,636 | 12/1981 | Gordon | 424/1.1 |
| 4,452,773 | 6/1984 | Molday | 424/1.1 |
| 4,508,625 | 4/1985 | Graham | 424/101 |
| 4,577,636 | 3/1986 | Spears | 128/654 |
| 4,706,622 | 8/1985 | Cohen | 424/1.1 |

FOREIGN PATENT DOCUMENTS

| 71564 | 2/1983 | European Pat. Off. | 424/1.1 |
|---|---|---|---|
| 133603 | 2/1985 | European Pat. Off. | 424/1.1 |
| 169299 | 1/1986 | European Pat. Off. | 424/1.1 |
| 184899 | 6/1986 | European Pat. Off. | 424/1.1 |
| 186947 | 7/1986 | European Pat. Off. | 424/1.1 |
| 3022649 | 3/1982 | Fed. Rep. of Germany | 424/1.1 |
| 3316703 | 11/1984 | Fed. Rep. of Germany | 424/1.1 |
| 3443251 | 5/1986 | Fed. Rep. of Germany | 424/1.1 |
| 55160720 | 12/1980 | Japan | 252/408.1 |
| 58-10515 | 1/1983 | Japan | 424/1.1 |
| 59-195161 | 11/1984 | Japan | 424/1.1 |
| 8401503 | 4/1984 | World Int. Prop. O. | 424/1.1 |
| 8505554 | 12/1985 | World Int. Prop. O. | 424/1.1 |
| 8602841 | 5/1986 | World Int. Prop. O. | 424/1.1 |

OTHER PUBLICATIONS

Molday, R. S. et al., J. Immunol. Methods, vol. 52, No. 3, pp. 353–367 (8/13/82).
The Merck Index, Eighth Edition, Merck & Co., Inc., Rahway, N.J., p. 1063, "Transferrin" (1968).

Primary Examiner—Richard D. Lovering
Assistant Examiner—John M. Covert
Attorney, Agent, or Firm—Scully, Scott, Murphy & Presser

[57] ABSTRACT

This invention provides particle compositions possessing ferromagnetic, paramagnetic or diamagnetic properties. The particles are especially useful when used in the disease diagnostic and treatment regimens as described in U.S. Pat. Nos. 4,106,448, 4,136,683 and 4,303,636.

12 Claims, No Drawings

FERROMAGNETIC, DIAMAGNETIC OR PARAMAGNETIC PARTICLES USEFUL IN THE DIAGNOSIS AND TREATMENT OF DISEASE

CROSS REFERENCE TO RELATED APPLICATIONS

This application is a continuation-in-part of copending application U.S. Ser. No. 464,870, filed Feb. 8, 1983 and U.S. Ser. No. 559,229 filed Dec. 8, 1983, both of which are now abandoned this application being a continuation in part of U.S. patent application Ser. No. 731,551 filed May 7, 1985, now U.S. Pat. No. 4,735,796.

FIELD OF THE INVENTION

This invention relates to the field of diagnosis and treatment of disease and more specifically to the use of ferromagnetic, diamagnetic or paramegnetic particles for such diagnoses and treatment.

BACKGROUND OF THE INVENTION

The efficacy of minute particles possessing ferromagnetic, paramagnetic or diamagnetic properties for the treatment of disease, particularly cancer, has been described by R. T. Gordon in U.S. Pat. Nos. 4,106,488 and 4,303,636. As exemplified therein, ferric hydroxide and gallium citrate are used to form particles of a size of 1 micron or less and are introduced into cells in the area to be treated. All cells in the sample area are then subjected to a high frequency alternating electromagnetic field inductively heating the intracellular particles thus resulting in an increase in the intracellular temperature of the cells. Because the cancer cells accumulate the particles to a greater degree than the normal cells and further because of the higher ambient temperature of a cancer cell as compared to the normal cells; the temperature increase results in the death of the cancer cells but with little or no damage to normal cells in the treatment area. The particles are optionally used with specific cancer cell targeting materials (antibodies, radioisotopes and the like).

Ferromagnetic, paramagnetic and diamagnetic particles have also been shown to be of value for diagnostic purposes. The ability of said particles to act as sensitive temperature indicators has been described in U.S. Pat. No. 4,136,683. The particles may also be used to enhance noninvasive medical scanning procedures (NMR imaging).

As disclosed herein the particles of the subject invention are particularly useful in light of the references cited above.

BRIEF DESCRIPTION OF THE INVENTION

This invention relates to the use of pharmacologically acceptable ferromagnetic, paramagnetic and diamagnetic particles in the diagnosis and treatment of disease. The particles possess magnetic properties uniquely suited for treatment and diagnostic regimens as disclosed in U.S. Pat. Nos. 4,106,488, 4,136,683 and 4,303,636. Enhanced magnetic properties displayed by the particles disclosed herein include favorable magnetic susceptibility and characteristic magnetic susceptibility vs. temperature profiles. The enhanced magnetic properties displayed by the particles result in increased sensitivity of response to an electromagnetic field thereby permitting a more sensitive application of diagnostic and treatment modalities based thereon. A further benefit is derived from the chemical composition of said particles whereby intracellular accumulation and compartmentalization of the particles is enhanced which also contributes to the more sensitive application of diagnostic and treatment modalities. Particles useful in light of the subject invention comprise inorganic elements and compounds as well as organic compounds such as metal-dextran complexes, metal-containing prosthetic groups, transport or storage proteins, and the like. The organic structures may be isolated from bacteria, fungi, plants or animals or may be synthesized in vitro from precursors isolated from the sources cited above.

DETAILED DESCRIPTION OF THE INVENTION

This invention relates to the use of pharmacologically acceptable ferromagnetic, diamagnetic and parmagnetic particles in the treatment and diagnosis of disease. This invention relate to the synthesis and use of said particles which mediate and measure alterations of intracellular biophysical environment.

According to one form of the invention, selective treatment of cancer cells is achieved without damaging normal cells. The process comprises introducing minute particles into the interior of the cells of living tissue, these particles being injected intravenously while suspended in an appropriate solution are of a size generally having a diameter of approximately 1 micron or less and being of a material with properties, such as ferromagnetic, paramagnetic, or diamagnetic, so as to be inductively heated when subjected to a high frequency alternating electromagnetic field. Introducing the particles as described, the patient is thereafter subjected to an alternating electromagnetic field to inductively heat the particles sufficiently to raise the temperature of the cells by an increment of 8.0° to 9.5° centigrade thus killing the cancer cells without harming the normal cells. Further selectivity and increased affinity of the cancer cells for these particles may be achieved by incorporating specific radioisotopes or tumor specific antibodies bound to these particles.

When the ferromagnetic, diamagnetic or paramagnetic particles described above are employed as a cancer treating composition, the particle size of the particles should be not greater than about 1 micron. Preferable particle size would be less than the 1 micron size. When the minute particles described are to be injected intravenously into the patient, the use of any suitable compatible liquid vehicles is desirable. Aqueous solution of any such body-acceptable materials as dextran, dextrose, saline or blood, as well as water alone, can be used. The liquid vehicle should sustain the particles in suspension for the subsequent injection. Concentrations of such body-acceptable materials that may be useful are those that are up to about 50% by weight in water. Usually a solution of about 1% to 10% is adequate. The concentration of the particles in the solution is not critical and is usually in a range between 50 to 75 mg/cc of the solution.

The intravenous injection into the patient generally is in an amount such that between 1 to 10 mg of the particles per kg of body weight of the patient are injected at one time; however, up to approximately 20 to 45 mg total dosage per kg of body weight is possible. The greater weight of the patient, the higher the permissible dosage. The total amount of the dosage is not critical though 2 to 3 injections, may be injected within a 24 to 72 hour period. The time span for the injections may vary greatly for various patients and for various objectives. The minute particles contained in the aqueous medium are transported through the bloodstream and have been found to be phagocytized by the cancerous cells to a far greater degree than, and in fact in some cases to the possible exclusion of, their admittance into normal cells.

Electronmicrographs of the cancerous tissue have proven the selective pickup of the magnetic particles by the cancer cells.

It has been found that the intracellular temperature of the cells may be raised between 8.0° centigrade and 9.5° centigrade to cause death in the cancer cell without damage being caused to the normal cells.

The inductive heating of the minute particles is achieved by using an electronic oscillator operating in the high-frequency range which heats the particles by subjecting them to an intense high-frequency field within a large but otherwise conventional helical coil, field energy being converted to heat through hysteresis losses and the resistive dissipation of eddy currents. The helical inductive coil is of sufficient internal diameter to permit the patient to pass within and of such length to encompass the length of the patient. Generally, the interal diameter should be at least 2 feet, but preferably would be greater than 3-6 feet in diameter. No maximum diameter is known to exist except that required from practical and economical considerations. Diameters of inductive coils of greater than 6 feet have a preferential effect in the overall process by providing more uniform flux gradient to the patient.

The frequency of the electromagnetic alternating high frequency field will range from 1 hertz to 100 megahertz from 0.5 kilowatts per kilogram of patient body weight 0.75 kilowatts of power per 1.0 kilograms of body weight has been found to be particularly useful. In this power and frequency range, the coil is selected to produce from 200–1000 oersteds, preferably 550–650 oersteds.

The time necessary to inductively heat the minute particles held within the cells to be treated depends substantially upon the frequency and the power producing the alternating electromagnetic field and ultimately the strength of the field produced. In general, it has been found that subjecting the patient to 5 to 12 minutes or preferably 8 to 10 minutes of the alternating electromagnetic field would be adequate to bring about the necessary temperature rise of at least 8.0° centigrade and that the variables with respect to the type and concentration of the particles in the vehicle and the electromagnetic treatment are not critical provided that the necessary temperature is achieved.

In a further embodiment, the particles introduced intracellularly as described may be used as a method of delivering a chemotherapeutic agent primarily to the interior of the cancer cells by having the chemotherapeutic agent encapsulated within said particles and released at the proper time by application of the high frequency alternating electromagnetic field thus solubilizing the said particles within the cells.

These two embodiments are discussed in detail in U.S. Pat. Nos. 4,106,488 and 4,303,636 which are incorporated herein by reference.

It has recently been discovered that a wide range of ferromagnetic, paramagnetic and diamagnetic particles which possess enhanced magnetic characteristics and in combination with desirable structural properties are particularly useful in light of the applications described above.

Whereas the particles described in U.S. Pat. Nos. 4,106,488 and 4,303,636 were selected primarily on the basis of their size and their ability to be inductively heated; it is now appreciated that additional criteria must be considered when selecting a particle for a particular application. In selecting the particles of the instant invention the following magnetic and physical characteristic were evaluated: magnetic permeability, magnetic susceptibility, magnetic moment, Curie points, and thermal conductivity. Magnetic permeability is a property of materials modifying the action of magnetic poles placed therein and modifying the magnetic induction resulting when the material is subjected to a magnetic field and may be defined as the ratio of the magnetic induction in the substance to the magnetizing field to which it is subjected. Magnetic susceptibility is measured by the ratio of the intensity of magnetization produced in a substance to the magnetizing force of intensity of the field to which it is subjected. Magnetic moment is measured by the torque experienced when it is at right angle to a uniform field of unit intensity. The value for magnetic moment is given by the product of the magnetic pole strength by the distance between the two poles. The Curie point represents the temperature above which substances loose their ferromagnetic properties Thermal conductivity relates to the ability of a substance to transfer thermal energy and is known to be effective by temperature.

In addition to the physical and magnetic characteristics listed above, other parameters must be evaluated. For ease of consideration these additional parameters may be grouped in relation to the time course of treatment. For example certain evaluations as to the efficacy of a particular particle can be made prior to the introduction of said particle to the subject, but such as selection must be modified by considerations relating to the behavior of the particle during the treatment period, and finally consideration must also be given to post-treatment parameters.

Pre-treatment parameters to be considered comprise, an evaluation of the magnetic and physical properties of the particles, the composition and solution properties displayed by the particles, and route of administration of said particles. For example, if the particles are to be delivered by intraveneous injection it would be important for the particles to be in a stable colloidial suspension in aqueous media.

After introduction of the particles into the subject, the following parameters become important; biocompatibility and toxicity considerations, the rate and degree of cellular uptake of the particles, the specificity of said uptake, the subcellular localization of particles once they have been taken up by the cells, the modification of the magnetic properties as a result of intracellular localization, and the effect upon magnetic properties as a result of metabolic activity within cells. For example, sulfactants may be profitably employed to reduce surface tension, and mask groups contributing to zeta potentials thereby enhancing the uptake of particles by the cells. In reference to sub-cellular localization it is possible to specifically target particles to specific intracellular locales by constructing the particle in the form of a molecular analog (e.g., mimic) of an endogeneous compartmentalized cellular component. For example by forming particles containing porphyrin moieties and providing same to cells within the treatment area; the particles will accumulate within porphyrin-rich area within the cells, i.e., mitochondria or chloroplasts, and participate in the cellular reactions attendant thereto.

It is important to realize that as the structural complexity of the particle increases not only is size a consideration but also the overall shape and the conformation and configuration of various particle components must be considered. With reference to the porphyrin-containing particles mentioned above, it is known, for example, that the position of the metal value relative to the plane of the porphyrin ring has important consequences with respect to the metal's reactive properties. Further it must be appreciated that the type and position of the side chains on the porphyrin moiety can act to position the metal in a particular orientation and as a corollary, the metal will have an affect of the conformation of the side chains of the porphyrin as well.

The interactions at the particle surface-cellular environment interface are also important. For example, induced magnetic moments can result from the ordering which takes place at the particle surface.

Further particles which are subject to cellular metabolism will display a change in magnetic characteristic as a result of said metabolism. Although the intracellular effects upon metabolizable, organic metal-containing particles as described above are important considerations it should be remembered that the characteristics of less complex particles also affected by intracellular localization. For example, the inductive heating of the particles comprised of inorganic materials in suspension outside the cell; generally transmit their effect through hysteresis owing to their small size. However, after uptake of cells the individual particles tend to cluster providing an overal "group" particles size whereby heating due to eddy currents is also possible.

Thus, the subject invention not only provides an effective method for monitoring the treatment phase so as to allow for treatment techniques based upon limited increases in temperature (i.e., rises in temperature of 9.5° C.), but also provides for an additional treatment technique. In this further embodiment, since the subject invention provides a means for specific particle distribution and a sensing of the responsiveness to the various treatment fields, high temperature treatment modalities are also possible. The 9.5° C. limitation as discussed supra is, of course, predicated on the case situation in which particle distribution, magnetic state and orientation were equal in all cancer cells and normal cells under the treatment conditions. However, employing the improved methods of the subject invention thereby affecting specific particle distribution, orientation, differential magnetic susceptbility, timing and other parameters described herein, between the cancer cells and the normal cells within the target area, increases in the intracellular temperature up to 100° C. are possible without substantially damaging the surrounding normal cells.

Irreversible cell death and biological alterations are induced by the energy input to the particle and thereupon to the interior of the cancer cell. Thus, the same energy input may be accomplished by application over a long period of time with a consistent small temperature rise (8° to 9° C. for 10 to 20 minutes) or when the same total amount of energy is applied over a short period of time, a higher temperature results (100° C. for a few seconds).

Obviously, timing and energy parameters may be adjusted to provide a spectrum of intracellular temperature which may be utilized depending upon the treatment appropriate in specific cases.

Finally, with respect to post-treatment practice, consideration must be given to the removal of the particles from the subject. The removal is accomplished by natural excretory processes which may be supplemented with chelating agents or metal efflux stimulating compositions.

Although the effective electromagnetic fields referred to herein have been characterized as alternating electromagnetic fields, there is no evidence which would preclude the use of electromagnetic fields of the oscillating or pulsed type and such fields are contemplated by the subject invention.

Particularly useful particles include both inorganic elements and compounds as well as metal-containing organic compounds. Inorganic elements and compounds particularly well suited, owing to their favorable magnetic parameters, comprise elements, such as dysprosium, erbium, europium, gaolinium, holmium, samarium, terbium, thulium, ytterbium or yttrium and compounds thereof such as dysprosium sulfate, erbium sulfate, europium oxide, europium sulfate, gadolinium oxide, gadolinium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$) yttrium aluminum oxide ($Y_3Al_5O_{12}$), other dimetallic compounds such as dysprosium-nickel, dysprosium-cobalt, gadolinium-iron, ytterbium-iron, cobalt-samarium, gadolinium-yttrium, and dysprosium-gallium, and actinide series element and compounds thereof.

Metal-containing organic molecules useful for the application discussed above, comprise particles of iron-dextrans such as FeOOH-dextran or $Fe_3O_4$-dextran complexes and other dextran metal complexes wherein the metal is selected from the group comprising cobalt, zinc, chromium, nickel, gallium, platinum, manganese and rare earth metals such as dyprosium, erbium, europium, gadolinium holmium, samarium, terbium, thulium, ytterbium and yttrium, other dimetall compounds such as dysprosium-nickel, dysprosium-cobalt, gadolinium-iron, ytterbium-iron, cobalt-samarium, gadolinium-yttrium, and dysporsium hysprosium-gallium, actinide series elements and compounds, ferric ammonium citrate, and various iron transporting and chelating compounds such as enterochelin, hydroxamates, phenolates, ferrichromes, desferri-ferrichromes, ferritin, ferric mycobactins, and iron-sulfur proteins such as ferredoxin and rubredoxin.

Particularly appropriate metal-containing organic structures for use with the present invention are the metalloporphyrins such as etioporphyrins, measoporphyrins, uroporphyrins, coprophyrins, protoporphyrins, and dicarboxylic acid containing porphyrins and substituted porphyrins such as tetraphenylporphyrin sulfonate (TPPS). Especially advantageous protophoryrins comprise hematoporphyrins, chlorophylls, and cytochromes. In addition to the naturally occurring protoporphyrins which possess either iron or magnesium-containing moieties, mixed-metal or di-metal hybrid porphyrins may also be prepared. For example, by substituting an alternative metal for the iron in hematoporphyrin, the advantages of the porphyrin moiety (e.g., in terms of specificity of localization is retained while the unique magnetic properties of the new metal enhance the sensitivity of the substituted molecule. Suitable metals for purposes of substitution comprise cobalt, manganese, zinc, chromium, gallium, nickel, platinum and rare earth series of metals dysprosium, erbium, europium, gadolinium, holmium, samarium, terbium, thulium, ytterbium and ytterium, dimetallic compounds such as dysprosium-nickel, dysprosium-cobalt gadolinium-iron, ytterbium-iron, cobalt-samarium, gadolinium yttrium, dysprosium-gallium and actinide series elements and compounds thereof. The substituted porphyrins are then optionally reacted with dextran to form a metal-containing porphyrin dextran complex in particle form. Suitable porphyrin acceptors comprise any dicarboxylic acid containing porphyrin, such as protoporphyrins (e.g., hematoporphyrins), and the like.

The substitution reaction is carried out in vitro by reacting the desired metal with the desired porphyrin in the presence of the enzyme ferrochelatase (E.C. 4.99.1.1). Reaction conditions as described by Jones and Jones (Biochem. J 113:507–14 (1969) or Honeybourne, et al. (FEBS Lett.: 98:207–10(1979)) are suitable.

Particularly, advantageous particle systems include transferrin-based particle systems wherein the particle system comprises an $Fe_3O_4$-transferrin dextran as well as other metal-transferrin dextran complexes wherein the metal is selected from the group comprising cobalt, zinc, chromium, nickel, gallium, platinium, manganese and rare earth metals such as dyprosium, erbium, europium, gadolinium, holmium, samarium, terbium, thulium, ytterbium and yttrium, other dimetallic compounds such as dysprosium-nickel, dysprosium-cobalt, gadolinium-iron, ytterbium-iron, cobalt-samariu, gadolinium-yttrium, and dysprosium-gallium, actinide series elements and compounds. Additionally, metalloporphyrin-transferrin wherein the metalloporphyins are those mentioned above.

Further useful particle systems include antibody-ferritin-$Fe_3O_4$ complexes and other antibody-ferritin based systems where the $Fe_3O_4$ is optionally substituted with a transition metal, rare earth metal, metalloporphyrin or other ferromagnetic, diamagnetic or paramagnetic particle wherein the antibody is of monoclonal or polyclonal origin and is specifically reactive to the specific target organ or cell-type desired.

Metallothionein-based particle systems and lectin-based systems are also useful. In these systems either the metallothionein or lectin is used in combination with $Fe_3O_4$ or the transition metal, rare earth metal, metalloporphyrin and ferromagnetic, diamagnetic or paramagnetic particles as described above.

Specific metal-organic compound complexes are given in Table I.

TABLE I

Particle Complexes

Fe(III) Tetraphenylporphyrin sulfonate (TPPS$_4$) Acetate
Fe(III) TPPS$_4$Acetate 4Na Salt (H$_2$O)
Fe(III) Mesoporphyrin IX Chloride
Fe(III) TPPS$_4$ Chloride
Co TPPS$_4$
Co(III) MesoTPPS$_4$ Tetra Na Salt (acetate)
Fe Phthalocyanine Tetrasulfonate Tetra sodium salt
Tetra Sodium-meso-Tetra (4-sulfonato-phenyl) Porphine (12 hydrate)
Fe(III) Tetra (N-Methyl 4-Puridyl) Porphyrin Pentachloride
Fe Phthalocyanine
Hemin
Fe-Hematoporphyrin D. (HPD)
Fe-Acetoxyethyl vinyl Deuteroporphyrin
Fe-Protoporphyrin IX
Fe-Deuteroporphyrin 2,4 bis acetal
Mn-TPPS$_4$
Co-N$^+$MTPyP
Mn-N$^+$MTPyP
Co-Mesoporphyrin X
Protohemin
Deuterohemin
Meso-tetra (4-N methyl pyridyl) hemin tetraiodide
Meso-tetra (4-carboxy phenyl) hemin
Ni-TPPS
Ni-HPD
Mn-Mesoporphyrin IX
Co-Protoporphyrin IX
Mn-Protoporphyrin IX
Sn-Protoporphyrin IX
Co-HPD
Mn-HPD
Gd-TPPS
Gd-HPD
Hematoporphyrin Mono-acetate-Fe
Ferretin-Fe
Ferredoxin-Fe(4)
Transferrin-Fe
Hematoporphyrin Diacetate-Gd
GdFe$_2$-TPPS$_4$
GdFe$_2$-HPD
FeTPPS$_4$(OH$_2$)$_2$]ClO$_4$—
FeTPP(OH$_2$)$_2$]ClO$_4$—
Bisimidozole (FeTPPS)ClO$_4$—
Fe-nitrolacetate
Fetetrasulfinated phalocyanine
Rubrium-ferricytochrome/c According to another embodiment of the invention, the ferromagnetic, paramagnetic or diamagnetic particles described above are used for diagnostic purposes whereby the magnetic characteristics of said particles are correlated with the intracellular temperature of the cells within the sample area. Experimental details of this application may be found in U.S. Pat. No. 4,136,683 which is incorporated herein by reference.

One magnetic characteristic known to be temperature dependent is magnetic susceptibility. Magnetic susceptibility is measured by the ratio of the intensity of magnetization produced in a substance to the magnetizing force or intensity of the field to which it is subjected. This magnetic characteristic is routinely measured by magnetometer devices, such as a vibrating magnetometer or a flux gate magnetometer. Therefore, by measuring the magnetic susceptibility of particles at various temperatures, it is quite simple to calibrate the magnetometer equipment so that when it measures the magnetic susceptibility of the particles a simple calibration will indicate the exact corresponding temperature of the particle.

By way of illustrating the increased magnetic susceptibility of some of the elements or compounds described above, the following table is provided:

| Element or Compound | Temp (°K.) | Mag. Sus. ($10^6$ cgs) |
|---|---|---|
| Iron Oxide (ref.) | 293 | +7,200 |
| Dysprosium Oxide | 287.2 | +89,600 |
| Dysprosium Sulfate | 291.2 | +92,760 |

-continued

| Element or Compound | Temp (°K.) | Mag. Sus. ($10^6$ cgs) |
|---|---|---|
| Octahydrate | | |
| Erbium Oxide | 286 | +73,920 |
| Erbium Sulfate Octahydrate | 293 | +74,600 |
| Europium | 293 | +34,000 |
| Europium Oxide | 298 | +10,100 |
| Europium Sulfate | 293 | +25,730 |
| Holmium Oxide | 293 | +88,100 |
| Holmium Sulfate Octahydrate | 293 | +91,600 |
| Terbium | 273 | +146,000 |
| Terbium Oxide | 288.1 | +78,340 |
| Terbium Sulfate Octahydrate | 293 | +76,500 |
| Thulium | 291 | +25,500 |
| Thulium | 296.5 | +51,444 |
| Ytterbium Sulfide | 292 | +18,300 |

Thus, the enhanced magnetic characteristics displayed by the particles of the subject invention results in an increase in the sensitivity of response of said particles in an electromagnetic field thereby increasing the overall sensitivity and control of the various diagnostic and treatment modalities based thereon.

A further benefit is derived from the fact that some particle compositions comprise a ferromagnetic, paramagnetic or diamagnetic component integrated into a cell or organelle specific molecular structure, thereby permitting efficient targeting and delivery of said particles to specific intracellular compartments such as mitochondria, chloroplasts, nuclei, vacuoles and the like.

EXAMPLE

Preparation of $Fe_3O_4$-Dextran-Transferrin Particles

An Fe-transferrin particle colloidal solution was prepared by combining 0.00638 g $Fe(NH_4)_2(SO_4)_2 \cdot 6H_2O$ water solution with 0.00806 g citric acid, 1.0 cc of a 1M sodium phosphate solution in water and 99 cc of water, the pH adjusted to 7.4 with dilute sodium hydroxide or hydrochloric acid and 1 cc of the combination added to 10 mg of human transferrin obtained from Cappel Laboratories to obtain an Fe-transferrin composition. The Fe-transferrin was dialyzed against a 0.01M sodium phosphate water solution adjusted to pH 7.4 and a pure Fe-transferrin particle composition obtained. The dialysis was performed against a cellophane membrane.

An iron oxide dextran particle having a particle size of less than one micron was prepared by mixing 10 cc of 50% Dextran T-40 with 10 cc of an aqueous solution containing 1.51 g $FeCl_3 \cdot 6H_2O$ and 0.64 g $FeCl_2 \cdot 4H_2O$. This mixture was stirred and titrated to pH 10.5 by the addition of 7.5% $NH_4OH$ and heated to 60° C. in a water bath for 20 minutes. Particles of $Fe_3O_4$-dextran were obtained and removed by centrifugation at a force of 600 g for 5 minutes. The particles are contained in the supernatant and the supernatant subjected to the same centrifugation two more times. The particles were then separated by taking the supernatant from the centrifuge and contacting it with a chromatographic column comprising Sephacryl 300 (obtained from the Pharmacia Company). The column was eluted with an aqueous buffer of 0.1M $NaC_2H_3O_2$ mixed with 0.15M NaCl adjusted to a pH of 6.5. The $Fe_3O_4$-dextran particles were thus removed by the elution step.

The $Fe_3O_4$-dextran particles were then oxidized by mixing 5 cc of the particles at a concentration of 10 mg/cc as a colloidal solution in aqueous $NaC_2H_3O_2$/-NaCl buffer with 5 mM $NaIO_4$ and were stirred for one hour at 25° C. This mixture was dialyzed against a 20 mM sodium borate water solution at a temperature of 4° C. and a pH of 8.5. The dialysis was conducted against a cellophane membrane. After the dialysis, the $Fe_3O_4$-dextran particles were recovered and 5 cc of these particles in suspension in the aforesaid $NaC_2H_3O_2$/NaCl buffer (the particles being at a concentration 10 mg/cc) 1 cc of the Fe-transferrin particles and 4.72 mg of sodium borohydride as an aqueous 0.25M solution were mixed for 5 minutes to produce Fe-dextran-transferrin particles after which this mixture was contacted with a Sephacryl 300 chromatographic column to remove any Fe-dextran particles. The column was eluted with 20 mM of a sodium phosphate buffer containing 0.15M NaCl at a pH of 7.4. The product eluted from the column comprised $Fe_3O_4$-dextran-transferrin particles. These particles were assayed for protein via the Biuret reaction (Bovine Serum Albumin standard). Iron was analyzed by means of a Carey 14 spectrophotometer and it was determined that the peak of the protein concentration corresponded to the peak of the colored Fe adsorption after the Sephacryl 300 separation indicating the transferrin had coupled to the iron-dextran particle.

When the $Fe_3O_4$-dextran-transferrin particles are contacted with a Phenyl-Sepharose column (in lieu of the Sepharyl 300 column) the $Fe_3O_4$-dextran-transferring particles remain attached while the $Fe_3O_4$-dextran particles pass through. Subsequently, the $Fe_3O_4$-dextran-transferrin particle is eluted off the column by lowering the ionic strength e.g. by contacting the column with water or using an ion with a less salting-out effect or increased chaotropic effect on altering the pH all of which is known in the art.

Electrophoresis may also be used to isolate the $Fe_3O_4$-dextran-transferrin particles from the $Fe_3O_4$-dextran particles.

The $Fe_3O_4$-dextran-transferrin particles thus obtained are used in the treatment and diagnosis of disease as described herein and have a particles size of less than about 1 micron in diameter.

What is claimed is:

1. A method of manufacturing a metal-transferrin dextran compound comprising producing a metal transferrin compound by combining a solution of a metal salt with transferrin to obtain said metal transferrin compound; producing a metal dextran compound by combining a solution of a metal salt with dextran to obtain said metal dextran compound and combining said metal transferrin compound with said metal dextran compound to obtain said metal-transferrin dextran compound.

2. The method of claim 1 wherein said metal-transferrin dextran compound is $Fe_3O_4$- transferrin dextran produced by combining an aqueous solution of an iron salt with transferrin to obtain an iron transferrin compound; combining an aqueous solution of an iron salt with dextran, oxidizing the iron salt to $Fe_3O_4$ to obtain $Fe_3O_4$ dextran and combining the iron transferrin with the $Fe_3O_4$ dextran to obtain $Fe_3O_4$transferrin dextran.

3. The method of claim 2 where said iron-transferrin and said $Fe_3O_4$ dextran are obtained as particles and said $Fe_3O_4$-transferrin dextran particles less than about 1 micron in diameter.

4. The method of claim 2 where said $Fe_3O_4$ dextran is further oxidized prior to combining with said iron transferrin.

5. The method of claim 1 where said metal-transferrin compound and said metal dextran compound are combined in the presence of a reducing agent to form said metal-transferrin dextran compound.

6. The method of claim 2, 3 or 4 where said iron-transferrin compound and said $Fe_3O_4$ dextran compound are combined in the presence of a reducing agent to form said $Fe_3O_4$-transferrin dextran.

7. The method of claim 1 or 5 where said metal transferrin compound and said metal dextran compound are dialyzed before they are combined to form said metal-transferrin dextran compound.

8. The method of claim 6 where said iron-transferrin compound and said $Fe_3O_4$ dextran compound are dialyzed before they are combined to form said $Fe_3O_4$-transferrin dextran compound.

9. The method of claim 1 or 5 where said metal of said metal-transferrin compound, said metal dextran compound and said metal-transferrin dextran compound is selected from the metals of Group VIII of the Periodic Table of Elements.

10. The method of claims 1 or 5 where said metal of said metal-transferrin compound, said metal dextran compound and said metal-transferrin dextran compound comprises iron.

11. The method of claim 7 where said metal of said metal transferrin compound, said metal dextran compound and said metal-transferrin dextran compound is selected from the metals of Group VIII of the Periodic Table of Elements.

12. The method of claim 7 where said metal of said metal-transferrin compound, said metal dextran compound and said metal-transferrin dextran compound comprises iron.

* * * * *

UNITED STATES PATENT AND TRADEMARK OFFICE
CERTIFICATE OF CORRECTION

PATENT NO. : 5,043,101

DATED : August 27, 1991

INVENTOR(S) : Robert T. Gordon

It is certified that error appears in the above-identified patent and that said Letters Patent is hereby corrected as shown below:

Column 10, line 64, Claim 3: "dextran particles" should read as --dextran is obtained as particles--

Signed and Sealed this

Second Day of March, 1993

Attest:

STEPHEN G. KUNIN

*Attesting Officer*      Acting Commissioner of Patents and Trademarks